United States Patent
Young et al.

(10) Patent No.: US 8,776,575 B2
(45) Date of Patent: Jul. 15, 2014

(54) IMPACT TEST FIXTURES

(75) Inventors: Jonathan Richard Young, Dundee, MI (US); Ronald Alonzo Bowers, New Hudson, MI (US); Justin Thomas Lenoir, Fenton, MI (US)

(73) Assignee: Toyota Motor Engineering & Manufacturing North America, Inc., Erlanger, KY (US)

( * ) Notice: Subject to any disclaimer, the term of this patent is extended or adjusted under 35 U.S.C. 154(b) by 282 days.

(21) Appl. No.: 13/296,652

(22) Filed: Nov. 15, 2011

(65) Prior Publication Data

US 2013/0118226 A1  May 16, 2013

(51) Int. Cl.
*G01M 7/00* (2006.01)

(52) U.S. Cl.
USPC .................................................. 73/12.01

(58) Field of Classification Search
USPC .................................................. 73/12.01
See application file for complete search history.

(56) References Cited

U.S. PATENT DOCUMENTS

| | | | |
|---|---|---|---|
| 5,483,845 A | 1/1996 | Stein et al. | |
| 5,485,758 A | 1/1996 | Brown et al. | |
| 5,861,544 A | 1/1999 | Kosaraju et al. | |
| 5,872,321 A | 2/1999 | Yannaccone | |
| 5,929,348 A | 7/1999 | Stein et al. | |
| 6,178,805 B1 | 1/2001 | Kosaraju et al. | |
| 6,256,601 B1 | 7/2001 | Wipasuramonton et al. | |
| 6,427,520 B2 | 8/2002 | Kim | |
| 6,533,319 B1 * | 3/2003 | Denby et al. | 280/759 |
| 6,609,409 B1 | 8/2003 | Bock et al. | |
| 6,988,560 B2 * | 1/2006 | Bay | 172/272 |
| 6,990,845 B2 | 1/2006 | Voon et al. | |
| 7,610,821 B2 | 11/2009 | Klein | |
| 7,775,082 B2 * | 8/2010 | Friedman et al. | 73/12.06 |
| 8,327,693 B2 * | 12/2012 | Scherbring | 73/84 |
| 8,511,139 B2 * | 8/2013 | Lane et al. | 73/12.13 |
| 2001/0003920 A1 | 6/2001 | Kim | |

* cited by examiner

*Primary Examiner* — Lisa Caputo
*Assistant Examiner* — Octavia D. Hollington
(74) *Attorney, Agent, or Firm* — Dinsmore & Shohl LLP

(57) ABSTRACT

An impact test fixture includes a rolling frame structure, a ballast attachment feature coupled to the rolling frame structure, a position-adjustable attachment assembly coupled to the rolling frame structure, and a specimen attachment member coupled to the position-adjustable attachment assembly. The specimen attachment member is adjustable in a vertical direction and a transverse direction relative to the rolling frame structure.

19 Claims, 5 Drawing Sheets

IMPACT TEST FIXTURES

TECHNICAL FIELD

The present disclosure is generally directed to impact test fixtures and, more specifically, impact test fixtures having position-adjustable attachment assemblies and ballasts.

BACKGROUND

Motor vehicles incorporate energy absorbing structures that are designed to deform to absorb kinetic energy due to the motor vehicle colliding with another object. The energy absorbing structures deform when impacted, and the deformation of the energy absorbing structures reduce the amount of energy that can be imparted to the passenger cabin and to the passengers of the motor vehicle.

Previous attempts at testing the energy absorbing structures have been inadequate. Component level testing, for example "drop tower" testing, generally rigidly mounts the energy absorbing structure and introduces a weighted object in an attempt to simulate a motor vehicle collision. However, component level testing does not generally replicate the boundary conditions the energy absorbing structure experiences in a motor vehicle collision. Full scale motor vehicle testing, where the energy absorbing structure is mounted to the motor vehicle, can accurately replicate the boundary conditions on the energy absorbing structure. However, full scale motor vehicle testing incurs a high cost and time for preparation.

Accordingly, impact test fixtures that replicate boundary conditions of a motor vehicle collision are required.

SUMMARY

In one embodiment, an impact test fixture includes a rolling frame structure, a ballast attachment feature coupled to the rolling frame structure, a position-adjustable attachment assembly coupled to the rolling frame structure, and a specimen attachment member coupled to the position-adjustable attachment assembly.

In another embodiment, an impact test fixture includes a rolling frame structure and a ballast attachment feature coupled to the rolling frame structure. The impact test fixture also includes a frame-side fixturing element coupled to the rolling frame structure, a specimen-side fixturing element coupled to the frame-side fixturing element, stays coupled to the specimen-side fixturing element, and a specimen attachment member coupled to the stays. The frame-side fixturing element and/or the specimen-side fixturing element are adjustable in at least one of a vertical direction or a transverse direction relative to the rolling frame structure such that the specimen attachment member is adjustable in the vertical direction and the transverse direction relative to the rolling frame structure.

In yet another embodiment, an impact test fixture for simulating motor vehicle conditions on a specimen includes a rolling frame structure having a center of gravity, a ballast attachment feature coupled to the rolling frame structure, the ballast attachment feature securing ballast weights to the rolling frame structure. The impact test fixture also includes a position-adjustable attachment assembly coupled to the rolling frame structure, and a specimen attachment member coupled to the position-adjustable attachment assembly, where the specimen attachment member secures the specimen to the impact test fixture. The specimen attachment member is movable in a vertical direction and a transverse direction to adjust a position of the specimen relative to the center of gravity of the rolling frame structure.

These and additional features provided by the embodiments described herein will be more fully understood in view of the following detailed description, in conjunction with the drawings.

BRIEF DESCRIPTION OF THE DRAWINGS

The embodiments set forth in the drawings are illustrative and exemplary in nature and not intended to limit the subject matter defined by the claims. The following detailed description of the illustrative embodiments can be understood when read in conjunction with the following drawings, where like structure is indicated with like reference numerals and in which:

DETAILED DESCRIPTION

Figure 1:
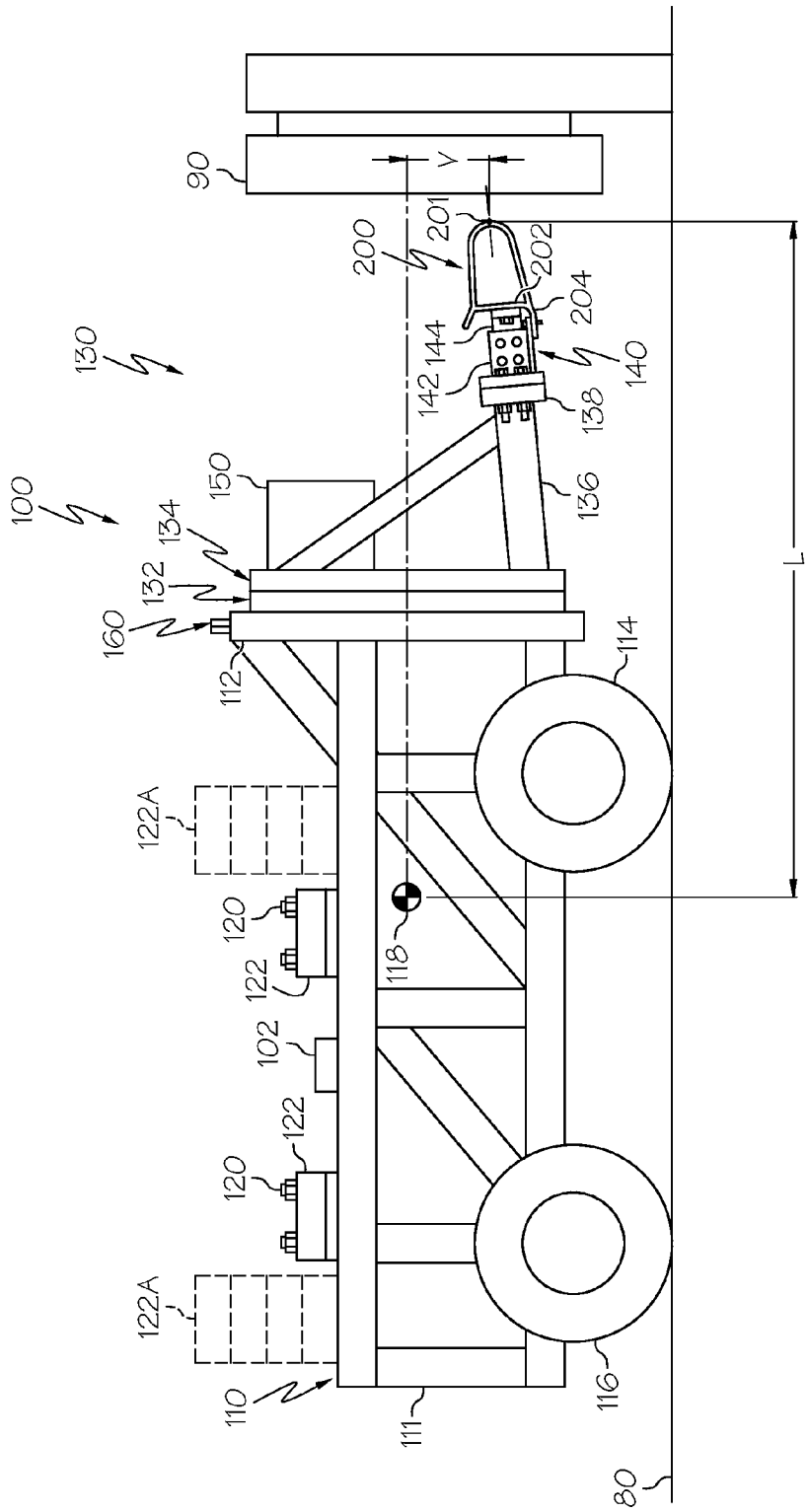
FIG. 1 depicts a side view of an impact test fixture according to one or more embodiments shown and described herein.

Referring to FIG. 1, an impact test fixture for replicating the boundary conditions of a motor vehicle impact on a specimen is depicted. The impact test fixture includes a rolling frame structure having a ballast attachment mechanism, a position-adjustable attachment assembly coupled to the rolling frame structure, and a specimen attachment member coupled to the position-adjustable attachment assembly. The specimen attachment member includes components that replicate the attachment features of the motor vehicle so as to replicate the attachment of the specimen to the motor vehicle. The position-adjustable attachment assembly is adjustable relative to the center of gravity of the impact test fixture so as to replicate the location of the specimen to the center of gravity of the motor vehicle. The position of the ballast is adjustable on the rolling frame structure to match the rotational inertia of the motor vehicle. The impact test fixture will be described in more detail herein with specific reference to the appended drawings.

Referring to FIG. 1 in detail, an impact test fixture 100 for testing an automotive component includes a rolling frame structure 110, a position-adjustable attachment assembly 130, and a specimen attachment member 140. The rolling frame structure 110 includes a space-frame 111, a forward wheel set 114 and a rear wheel set 116. The forward wheel set 114 and the rear wheel set 116 roll along a ground surface 80, allowing the impact test fixture 100 to translate towards a barrier 90 during an impact test. The position-adjustable attachment assembly 130 is coupled to a forward rail member 112 of the rolling frame structure 110.

The rolling frame structure 110 includes at least one ballast attachment feature 120. Ballast 122 may be secured to the rolling frame structure 110 at the ballast attachment features 120 such that the mass of the impact test fixture 100 replicates the mass of a motor vehicle. The addition of ballast 122 to the rolling frame structure 110 may change the position of the center of gravity 118 of the impact test fixture 100 in the vertical direction (i.e., the direction of V), the transverse direction (i.e., the direction of T of FIG. 2), and the lateral direction (i.e., the direction of L). The ballast attachment features 120 may each include a threaded rod that is secured to the space-frame 111 of the rolling frame structure 110. The ballast 122 may therefore be secured to the rolling frame structure 110 by tightening a nut along the threaded rod. The position and amount of the ballast 122, 122A can be modified such that the rotational inertia of the impact test fixture 100 is closely matched to the motor vehicle. In some embodiments, the ballast attachment features 120 are repositionable in the lateral direction (i.e., the direction of L) of the rolling frame structure 110 to allow for the desired placement of the ballast 122, 122A. In other embodiments, a plurality of ballast attachment features 120 are coupled to the rolling frame structure 110 to allow for the desired placement of the ballast 122, 122A.

Figure 2:
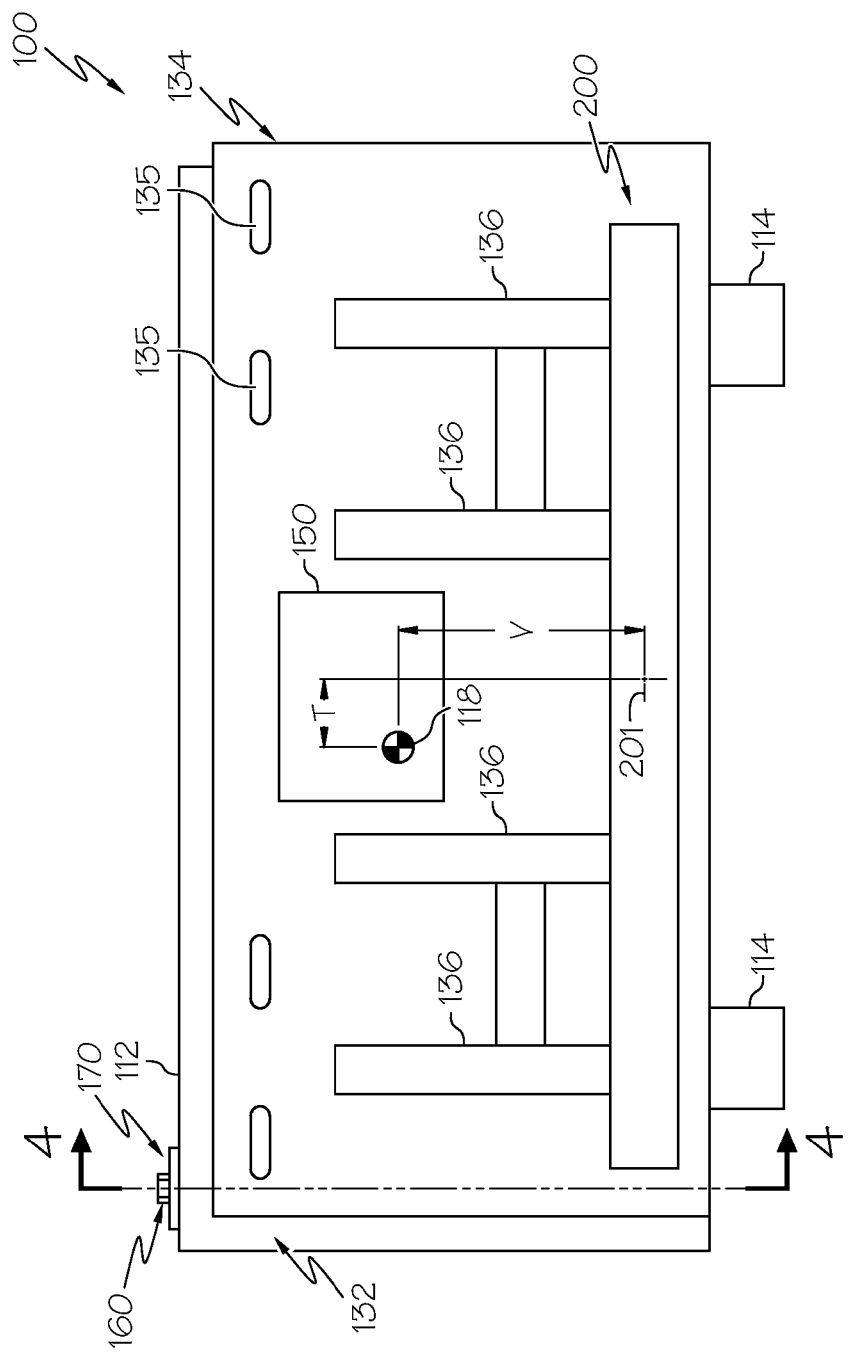
FIG. 2 depicts a front view of an impact test fixture according to one or more embodiments shown and described herein.
Figure 3:
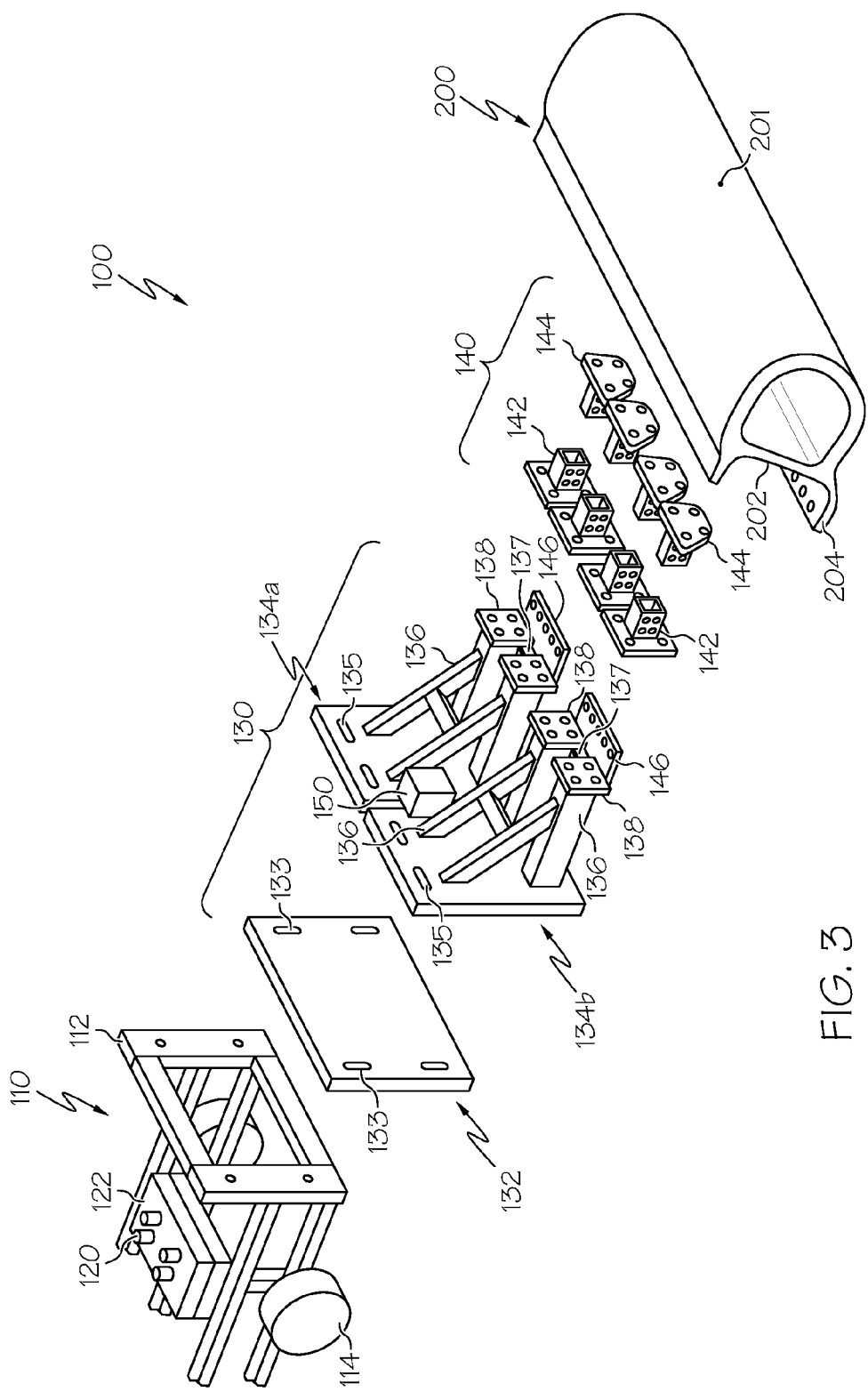
FIG. 3 depicts an exploded perspective view of an impact test fixture according to one or more embodiments shown and described herein.

Referring to FIGS. 1-3, embodiments of the position-adjustable attachment assembly 130 include a frame-side fixturing element 132 and a specimen-side fixturing element 134. In some embodiments, the position-adjustable attachment assembly 130 may be divided into two parts: a first specimen-side fixturing element 134a and a second specimen-side fixturing element 134b as depicted in FIG. 3. This two-part design permits the first and second specimen-side fixturing elements 134a, 134b to be repositioned with respect to one another thereby enabling the replication of different automobile attachment points. The frame-side fixturing element 132 includes a plurality of vertical attachment channels 133. The vertical attachment channels 133 allow the frame-side fixturing element 132 to be coupled to the rolling frame structure 110 while maintaining adjustability of the frame-side fixturing element 132 in the vertical direction relative to the forward rail member 112 of the rolling frame structure 110. Similarly, the specimen-side fixturing element 134 illustrated in FIGS. 1 and 2, and the first and second specimen-side fixturing elements 134a, 134b illustrated in FIG. 3, include a plurality of horizontal attachment channels 135. The horizontal attachment channels 135 allow the specimen-side fixturing elements 134, 134a, 134b to be coupled to the rolling frame structure 110, while allowing the specimen-side fixturing elements 134, 134a, 134b to be adjustable in the transverse direction T relative to the frame-side fixturing element 132. Further, the horizontal attachment channels 135 allow for adjustability of the spacing between the first and second specimen-side fixturing elements 134a, 134b.

While mention has been made herein to the positioning of the vertical attachment channels 133 and the horizontal attachment channels 135 to the frame-side fixturing element 132 and the specimen-side fixturing elements 134, 134a, 134b, it should be understood that other orientations that provide transverse direction T and vertical direction V adjustment of the specimen-side fixturing elements 134, 134a, 134b relative to the rolling frame structure 110 are envisioned.

As illustrated in FIGS. 1 and 2, a specimen 200 coupled to the impact test fixture 100 will contact a barrier 90 at an impact location 201. In the embodiments described herein, the specimen 200 is an energy absorbing structure that is incorporated into a motor vehicle to disperse kinetic energy introduced to the specimen 200 when the motor vehicle collides with an object. As illustrated in FIGS. 1-3, the specimen 200 is a side sill that is installed along the sides of the motor vehicle at a position generally below the passenger egress doors. The impact test fixtures 100 illustrated in FIGS. 1-3 are generally configured to test the specimen 200 in a side-impact test. However, other components and test configurations are contemplated which may be used in conjunction with an impact test fixture 100.

Referring to FIGS. 1 and 2, to replicate the boundary conditions of a specimen 200 installed in a motor vehicle, the impact location 201 of the specimen 200 is located at a lateral distance L, a vertical distance V, and a transverse distance T away from the center of gravity 118 of the impact test fixture 100. The lateral distance L, the vertical distance V, and the transverse distance T replicate the corresponding lateral, vertical, and transverse distances the impact location 201 would be spaced from the center of gravity 118 of motor vehicle if the specimen 200 were installed on the motor vehicle. By replicating the spacing between the impact location 201 and the center of gravity 118 of the impact test fixture 100, boundary conditions of the motor vehicle undergoing a collision can be more accurately replicated. As discussed above, the position and the amount of ballast 122, 122A that is coupled to the impact test fixture 100 can be adjusted to change the rotational inertia of the impact test fixture 100. For example, an impact test fixture 100 having ballast 122 installed towards the center of the rolling frame structure 110 will have a lower rotational inertia than an impact test fixture 100 having ballast 122A installed towards the front and rear of the rolling frame structure 110. The position and the location of the ballast 122, 122A coupled to the rolling frame structure 110 can be modified such that the rotational inertia of impact test fixture 100 matches the rotational inertia of the motor vehicle. By matching the rotational inertia of the impact test fixture 100 to the motor vehicle, the rotational kinematics associated with an impact on the specimen 200 installed in the motor vehicle can be replicated by testing the specimen 200 on the impact test fixture 100. The position and location of the ballast 122, 122A, along with the position of the impact location 201 relative to the center of gravity 118 of the impact test fixture 100 can be determined by comparison with a computer model of the motor vehicle that the specimen 200 is associated.

Figure 4:
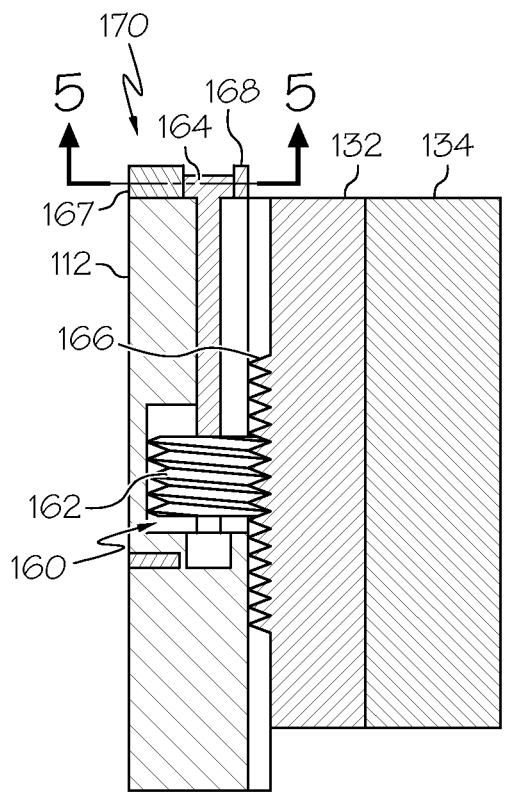
FIG. 4 depicts a sectional side view of the impact test fixture of FIG. 2 shown along line 4-4.
Figure 5:
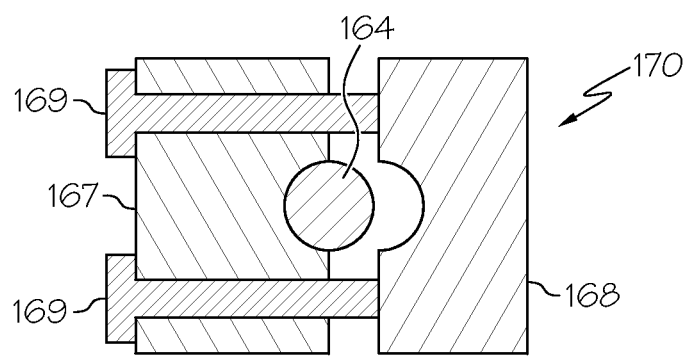
FIG. 5 depicts a sectional top view of the impact test fixture of FIG. 4 shown along line 5-5.

Referring again to FIG. 2, in some embodiments of the impact test fixture 100, the position-adjustable attachment assembly 130 includes an adjustment mechanism 160 that assists with positioning the specimen 200 such that the impact location 201 of the specimen 200 is located at the desired vertical distance V away from the center of gravity 118 of the impact test fixture 100. The adjustment mechanism 160, shown in detail in FIGS. 4 and 5, includes an externally-accessible adjustor 164 and a worm gear 162 located in a recess in the forward rail member 112. The worm gear 162 is meshed with a pinion 166 that is coupled to the frame-side fixturing element 132. Rotating the externally-accessible adjustor 164 rotates the worm gear 162, which translates the frame-side fixturing element 132 and the specimen-side fixturing element 134 in the vertical direction V. The frame-side fixturing element 132 may be secured to the forward rail member 112 by fasteners inserted through the vertical attachment channels 133. Such fasteners may prevent force from being transferred through the worm gear 162 and the pinion 166 during an impact test. The adjustment mechanism 160 also includes a stress relief mechanism 170. The stress relief mechanism 170 includes a back plate 167 and a head plate 168 having positions relative to one another controlled by load screws 169. When the frame-side fixturing element 132 and the specimen-side fixturing element 134 are positioned in the vertical direction V, the back plate 167 can be translated away from the head plate 168, drawing the worm gear 162 away from the pinion 166 on the frame-side fixturing element 132. By separating the worm gear 162 and the pinion 166 before an impact test, the likelihood of damage to the components of the adjustment mechanism 160 during an impact test is reduced.

Referring to FIGS. 1 and 2, the position-adjustable attachment assembly 130 also includes a plurality of stays 136 coupled to the specimen-side fixturing element 134. The stays 136 extend away from the specimen-side fixturing element 134. A variety of reinforcing members may be coupled to the specimen-side fixturing element 134 and/or the stays 136 to provide additional strength and stiffness to the stays 136. A stay adapter bracket 138 is coupled to the forward end of each of the stays 136. The stay adapter brackets 138 are adapted to couple the specimen attachment member 140 to the position-adjustable attachment assembly 130. The stay adapter brackets 138 are generally rigidly affixed to the position-adjustable attachment assembly 130.

Referring to FIGS. 1 and 3, the specimen attachment member 140 includes a plurality of stay interface sleeves 142 and a plurality of specimen attachment brackets 144. The stay interface sleeves 142 are adapted to be coupled to the stay adapter bracket 138. The specimen attachment brackets 144 are adapted to be coupled to the stay interface sleeves 142 and to the specimen 200 by fastening the specimen attachment brackets 144 to the abutment wall 202 of the specimen 200, as illustrated in FIG. 1. In some embodiments, the stay interface sleeves 142 are designed to be reused through multiple impact tests, and replaced when damaged, while the specimen attachment brackets 144 are designed to be consumed in one impact test. The specimen attachment brackets 144 are designed such that the shape and the strength of the specimen attachment brackets 144 replicate the shape and the strength of the attachment points of the motor vehicle. Therefore, the specimen attachment member 140, through the specimen attachment brackets 144, can replicate the boundary conditions the specimen 200 would experience if installed in a motor vehicle undergoing a collision. For example, the stiffness, the size and shape of the footprint of the specimen attachment brackets 144 that contact the specimen 200, and the attachment mechanism with the specimen attachment brackets 144 and the specimen 200 replicate the attachment with the specimen 200 and the motor vehicle. Because the specimen attachment brackets 144 are replaceable, a variety of specimen attachment brackets 144 representing the attachment points of the motor vehicle may be evaluated in impact tests using the impact test fixture 100.

Figure 6:
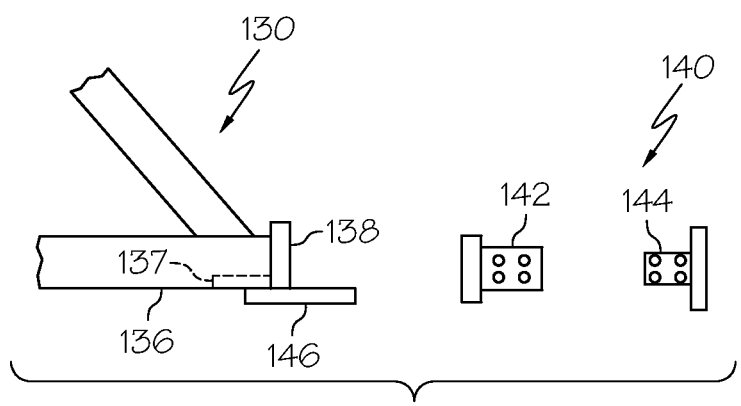
FIG. 6 depicts an exploded side view of a portion of an impact test fixture according to one or more embodiments shown and described herein.
Figure 7:
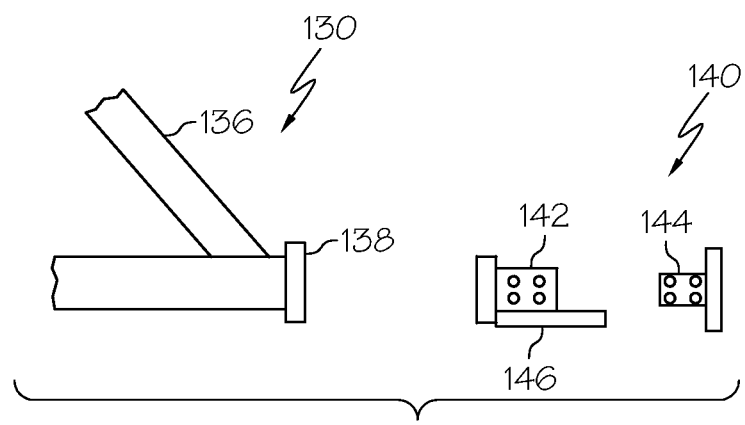
FIG. 7 depicts an exploded side view of a portion of an impact test fixture according to one or more embodiments shown and described herein.

Embodiments of the impact test fixture 100 may include cross-bridge interfaces 146 that extend in a transverse direction relative to the rolling frame structure 110. As illustrated in FIG. 1, the cross-bridge interfaces 146 are adapted to be coupled to the specimen 200 by fastening the cross-bridge interfaces 146 to a reinforcing flange 204 of the specimen 200. The cross-bridge interfaces 146 may be incorporated in the impact test fixture 100 to replicate the attachment points of the motor vehicle, where the specimen 200 would be fastened to the motor vehicle along the reinforcing flange 204. Therefore, the cross-bridge interfaces 146 can assist with replicating the boundary conditions the specimen 200 would experience if installed in a motor vehicle. As illustrated in FIGS. 3 and 6, some embodiments of the impact test fixture 100 include cross-bridge interfaces 146 that are coupled to the stays 136. A lateral support 137 may be coupled to the stays 136 and provide additional reinforcement to the cross-bridge interfaces 146. As illustrated in FIG. 7, other embodiments of the impact test fixture 100 may include cross-bridge interfaces 146 that are coupled to a portion of the specimen attachment member 140, for example the stay interface sleeves 142.

Referring again to FIG. 1, the impact test fixture 100 may also include a plurality of sensors 102 that can be monitored by a data acquisition system to determine parameters of an impact test. Examples of such sensors 102 include, but are not limited to, a speed sensor measuring a translation speed of the impact test fixture 100, a yaw rate sensor measuring the rate of rotation of the impact test fixture 100 about a vertical axis, a pitch rate sensor measuring the rate of rotation of the impact test fixture 100 about a horizontal axis, and a stroke sensor measuring ingress of the barrier 90 towards the impact test fixture 100 as the barrier 90 deforms the specimen 200.

The impact test fixture 100 may further include an energy absorbing damper 150 coupled to the specimen-side fixturing element 134 as depicted in FIG. 1. In the event the barrier 90 breaks through the specimen 200 during an impact test, the energy absorbing damper 150 is adapted to slow the speed of the impact test fixture 100 before the impact test fixture 100 contacts the barrier 90 thereby mitigating damages to the fixture. In one embodiment, the energy absorbing damper 150 comprises an aluminum honeycomb structure that is adapted to slow the speed of the impact test fixture 100 to zero velocity before the impact test fixture 100 contacts the barrier 90. The aluminum honeycomb structure is available from Hexcel Corporation of Stamford, Conn.

When the specimen 200 is coupled to the specimen attachment member 140, an impact test can be conducted using the impact test fixture 100 to replicate the boundary conditions that would be applied to the specimen 200 if it were installed in a motor vehicle undergoing a collision. The mass of the impact test fixture 100 allows an impact test to be conducted on the specimen 200 affixed to the impact test fixture 100 moving at the same speed as a motor vehicle, and transferring the same amount of kinetic energy to the specimen 200 as if it were attached to a motor vehicle. Replicating the speed of the impact test may assist with replicating the rate of strain deformation experienced by the specimen 200 as if the specimen 200 was installed in a motor vehicle. The lateral, vertical, and transverse dimensions between the impact location 201 and the center of gravity 118 of the impact test fixture 100 assist with replicating the forces applied to the specimen 200 by the pitch and yaw of the impact test fixture 100. These forces would be applied to the specimen 200 by the pitch and yaw of the motor vehicle. Further, the position and the amount of ballast 122, 122A coupled to the rolling frame structure 110 replicates the rotational inertia that is transferred to the specimen 200 as if the specimen 200 were attached to the motor vehicle. Additionally, the specimen attachment member 140 assists with replicating the attachment points of the motor vehicle. Replicating the attachment points of the motor vehicle increases the accuracy of testing of the specimen 200 using the impact test fixture 100, as the effect of the collision on the abutment wall 202 and the reinforcing flange 204 can be measured. Replicating the boundary conditions of the motor vehicle, including the rate of strain deformation, the pitch and yaw, and the attachment points, allows for testing of features of the specimen 200 to a high degree of accuracy without incurring the time or cost associated with conducting an impact test of a motor vehicle.

Additionally, during an impact test, components of the specimen attachment member 140, including the specimen attachment brackets 144, deform as the specimen 200 contacts the barrier 90. The specimen attachment brackets 144 allow identical attachments to be used in an impact test with the impact test fixture 100 that replicate the motor vehicle. The deformation of the specimen attachment brackets 144, therefore, accurately reflects the deformation of the attachment points of the motor vehicle, and thus replicates the boundary conditions of a motor vehicle impact test. By coupling the specimen attachment brackets 144 to the stay adapter brackets 138 with the stay interface sleeves 142, the specimen attachment brackets 144 can be removed from the impact test fixture 100 and replaced when attaching a specimen 200 for a subsequent impact test. Thus, the specimen attachment brackets 144 replicate the boundary conditions on the abutment wall 202 of the specimen 200 as if the specimen 200 were in a motor vehicle.

It should now be understood that an impact test fixture that replicates the boundary conditions of a motor vehicle impact on a specimen. The impact test fixture includes a position-adjustable attachment assembly that couples a specimen to the rolling frame structure. As ballast weights are added to and repositioned relative to the rolling frame structure, the center of gravity and the rotational inertia of the impact test fixture may shift. The adjustable attachment assembly can be moved such that the location of the specimen relative to the center of gravity of the impact test fixture replicates the location of the specimen relative to the center of gravity of the motor vehicle. An impact test can be conducted using the impact test fixture that replicates the pitch and yaw conditions exerted on the specimen by the motor vehicle.

It is noted that the terms "substantially" and "about" may be utilized herein to represent the inherent degree of uncertainty that may be attributed to any quantitative comparison, value, measurement, or other representation. These terms are also utilized herein to represent the degree by which a quantitative representation may vary from a stated reference without resulting in a change in the basic function of the subject matter at issue.

While particular embodiments have been illustrated and described herein, it should be understood that various other changes and modifications may be made without departing from the spirit and scope of the claimed subject matter. Moreover, although various aspects of the claimed subject matter have been described herein, such aspects need not be utilized in combination. It is therefore intended that the appended claims cover all such changes and modifications that are within the scope of the claimed subject matter.

What is claimed is:

1. An impact test fixture adapted to roll along a ground surface, the impact test fixture comprising:
    a rolling frame structure comprising a plurality of wheels for rolling along the ground surface;
    a ballast attachment feature coupled to the rolling frame structure;
    a position-adjustable attachment assembly coupled to the rolling frame structure;
    a specimen attachment member coupled to the position-adjustable attachment assembly, the position-adjustable attachment assembly comprises a frame-side fixturing element coupled to the rolling frame structure, a first specimen-side fixturing element coupled to the frame-side fixturing element, and a second specimen-side fixturing element coupled to the frame-side fixturing element; and at least one of the frame-side fixturing element or the first and second specimen-side fixturing elements is adjustable in at least one of a vertical direction and a transverse direction relative to the rolling frame structure such that the specimen attachment member is adjustable in the vertical direction and the transverse direction relative to the rolling frame structure.

2. The impact test fixture of claim 1, wherein a position of the ballast attachment feature on the rolling frame structure is adjustable.

3. The impact test fixture of claim 1, wherein:
    the position-adjustable attachment assembly comprises a frame-side fixturing element coupled to the rolling frame structure, and a specimen-side fixturing element coupled to the frame-side fixturing element; and
    at least one of the frame-side fixturing element or the specimen-side fixturing element is adjustable in at least one of a vertical direction and a transverse direction relative to the rolling frame structure such that the specimen attachment member is adjustable in the vertical direction and the transverse direction relative to the rolling frame structure.

4. The impact test fixture of claim 3 further comprising an adjustment mechanism adapted to adjust at least one of the frame-side fixturing element or the specimen-side fixturing element in the vertical direction.

5. The impact test fixture of claim 3, wherein the position-adjustable attachment assembly comprises:
    stays extending from the specimen-side fixturing element; and
    stay adapter brackets coupled to the stays.

6. The impact test fixture of claim 5, wherein the position-adjustable attachment assembly comprises at least one cross-bridge interface extending in the transverse direction and coupled to the stays.

7. The impact test fixture of claim 1, wherein the specimen attachment member comprises specimen attachment brackets coupled to stay adapter brackets.

8. The impact test fixture of claim 7, wherein the specimen attachment member further comprises stay interface sleeves coupled to the stay adapter brackets.

9. The impact test fixture of claim 8, wherein the specimen attachment member comprises at least one cross-bridge interface extending in a transverse direction and coupled to the stay interface sleeves.

10. The impact test fixture of claim 1 further comprising sensors measuring yaw and pitch of the rolling frame structure.

11. The impact test fixture of claim 1 further comprising an energy absorbing damper coupled to the rolling frame structure, wherein the energy absorbing damper is adapted to dissipate kinetic energy of the impact test fixture after a specimen dissipates kinetic energy of the impact test fixture.

12. An impact test fixture comprising:
    a rolling frame structure;
    a ballast attachment feature coupled to the rolling frame structure;
    a frame-side fixturing element coupled to the rolling frame structure;
    a specimen-side fixturing element coupled to the frame-side fixturing element;
    stays coupled to the specimen-side fixturing element; and
    a specimen attachment member coupled to the stays,
    wherein at least one of the frame-side fixturing element or the specimen-side fixturing element is adjustable in at least one of a vertical direction or a transverse direction relative to the rolling frame structure such that the specimen attachment member is adjustable in the vertical direction and the transverse direction relative to the rolling frame structure.

13. The impact test fixture of claim 12, wherein:
    the position-adjustable attachment assembly further comprises stay adapter brackets coupled to the stays; and the specimen attachment member comprises specimen attachment brackets that are coupled to the stay adapter brackets.

14. The impact test fixture of claim 12, wherein a position of the ballast attachment feature on the rolling frame structure is adjustable.

15. The impact test fixture of claim 12, wherein the specimen attachment member comprises at least one cross-bridge interface extending in the transverse direction and coupled to the stays.

16. An impact test fixture for simulating motor vehicle conditions on a specimen and adapted to roll along a ground surface, the impact test fixture comprising:
- a rolling frame structure comprising a plurality of wheels for rolling along the ground surface, the rolling frame structure having a center of gravity;
- a ballast attachment feature coupled to the rolling frame structure, the ballast attachment feature securing ballast weights to the rolling frame structure;
- a position-adjustable attachment assembly coupled to the rolling frame structure; and
- a specimen attachment member coupled to the position-adjustable attachment assembly, the specimen attachment member securing the specimen to the impact test fixture, wherein the specimen attachment member is movable in a vertical direction and a transverse direction to adjust a position of the specimen relative to the center of gravity of the rolling frame structure.

17. The impact test fixture of claim 16, wherein the position-adjustable attachment assembly comprises:
- a frame-side fixturing element coupled to the rolling frame structure;
- a specimen-side fixturing element coupled to the frame-side fixturing element; and
- stays extending from the specimen-side fixturing element.

18. The impact test fixture of claim 17, wherein:
- the position-adjustable attachment assembly further comprises stay adapter brackets coupled to the stays; and
- the specimen attachment member comprises specimen attachment brackets that are coupled to the stay adapter brackets.

19. The impact test fixture of claim 17, wherein the specimen attachment member comprises at least one cross-bridge interface extending in the transverse direction and coupled to the stays.

* * * * *